(12) United States Patent
Soucaille et al.

(10) Patent No.: US 8,168,434 B2
(45) Date of Patent: May 1, 2012

(54) **PROCESS FOR CHROMOSOMAL INTEGRATION AND DNA SEQUENCE REPLACEMENT IN *CLOSTRIDIA***

(75) Inventors: Philippe Soucaille, Deyme (FR); Rainer Figge, Le Crest (FR); Christian Croux, Auzeville Tolosane (FR)

(73) Assignee: Metabolic Explorer, Saint Beauzire (FR)

( * ) Notice: Subject to any disclaimer, the term of this patent is extended or adjusted under 35 U.S.C. 154(b) by 1082 days.

(21) Appl. No.: 11/737,025

(22) Filed: Apr. 18, 2007

(65) Prior Publication Data
US 2008/0085558 A1    Apr. 10, 2008

(30) Foreign Application Priority Data

Oct. 3, 2006  (WO) ................. PCT/EP2006/066997

(51) Int. Cl.
*C12N 15/74* (2006.01)
*C12N 1/21* (2006.01)
(52) U.S. Cl. .................................... 435/477; 435/252.3
(58) Field of Classification Search .................... None
See application file for complete search history.

(56) References Cited

FOREIGN PATENT DOCUMENTS

| WO | WO 01/71040 A2 | 9/2001 |
| WO | WO 01/77319 A2 | 10/2001 |
| WO | 2006/003412 | 1/2006 |

OTHER PUBLICATIONS

Reyrat, Inf. Imm., 1998, 66(9) 4011-7.*
Harris, et al.—Northern Morphological, and fermentation Analysis of spo0A Inactivation and over expression in *Clostridium acetobutylicum* ATCC 824, Journal of Bacteriology, vol. 184, No. 13, Jul. 2002, pp. 3586-3597, XPoo2415781.
Biswas,et al.—High-Efficiency Gene Inactivation and Replacement Systems for Gram-Positive Bacteria, Journal of Bacteriology, Washington, D.C. US, vol. 175, No. 11, Jun. 1, 1993, pp. 3628-3635, XP00563688.
Wilkinson, et al.—Targeted Integration of genes into the *Clostridium acetobutylicum* Chromosome, Microbiology, vol. 140, 1994, pp. 89-95, XP001248444.
Fabret, et al.—A new mutation delivery system for genome-scale approached in *Bacillus subtilis*, Molecular Microbiology, Blackwell Scientific, Oxford, GB, vol. 46, No. 1, Oct. 2, 2010, pp. 25-36, XP002315034.
Rood, et al.—Molecular Genetics and Pathogenesis of *Clostridium-perfringens*, Microbiological Reviews, vol. 55, No. 4, pp. 621-648, XP002415782.
International Search Report Jan. 22, 2007.
Datsenko et al.; "One-Step Inactivation of Chromosomal Genes in *Escherichia coli* K-12 Using PCR Products"; PNAS; Jun. 6, 2000; pp. 6640-6645; vol. 97; No. 12.
Mermelstein et al.; "In Vivo Methylation in *Escherichia coli* by the *Bacillus subtilis* Phage O3T I Mthyltransferase to Protect Plasmids From Restriction Upon Transformation of *Clostridium acetobutylicum* ATCC 824"; Applied and Environmental Microbiology, Apr. 1993; pp. 1077-1081; vol. 59; No. 4.

* cited by examiner

*Primary Examiner* — Nancy Vogel
(74) *Attorney, Agent, or Firm* — Baker Donelson Bearman Caldwell & Berkowitz, PC

(57) ABSTRACT

The present invention is related to a new method for replacing or deleting DNA sequences in *Clostridia*, with high efficiency, easy to perform and applicable at an industrial level. This method is useful to modify several genetic loci in *Clostridia* in a routine manner. This method is based on a replicative vector carrying at least two marker genes.

20 Claims, 4 Drawing Sheets

SEQUENCE LISTING

<160> NUMBER OF SEQ ID NOS: 36

<210> SEQ ID NO 1
<211> LENGTH: 34
<212> TYPE: DNA
<213> ORGANISM: Artificial
<220> FEATURE:
<223> OTHER INFORMATION: PCR primer

<400> SEQUENCE: 1
ctggcgccct gagtgcttgc ggcagcgtga gggg 34

<210> SEQ ID NO 2
<211> LENGTH: 33
<212> TYPE: DNA
<213> ORGANISM: Artificial
<220> FEATURE:
<223> OTHER INFORMATION: PCR primer

<400> SEQUENCE: 2
agcccgggga tctcatgctg gagttcttcg ccc 33

```
<210> SEQ ID NO 3
<211> LENGTH: 32
<212> TYPE: DNA
<213> ORGANISM: Artificial
<220> FEATURE:
<223> OTHER INFORMATION: PCR primer

<400> SEQUENCE: 3
tacaggcctt gagcgattgt gtaggctgga gc                                    32

<210> SEQ ID NO 4
<211> LENGTH: 33
<212> TYPE: DNA
<213> ORGANISM: Artificial
<220> FEATURE:
<223> OTHER INFORMATION: PCR primer

<400> SEQUENCE: 4
aacaggcctg ggatgtaacg cactgagaag ccc                                   33

<210> SEQ ID NO 5
<211> LENGTH: 24
<212> TYPE: DNA
<213> ORGANISM: Artificial
<220> FEATURE:
<223> OTHER INFORMATION: PCR primer

<400> SEQUENCE: 5
ccggggtacc gtcgacctgc agcc                                             24

<210> SEQ ID NO 6
<211> LENGTH: 25
<212> TYPE: DNA
<213> ORGANISM: Artificial
<220> FEATURE:
<223> OTHER INFORMATION: PCR primer

<400> SEQUENCE: 6
gaattccgcg agctcggtac ccggc                                            25

<210> SEQ ID NO 7
<211> LENGTH: 34
<212> TYPE: DNA
<213> ORGANISM: Artificial
<220> FEATURE:
<223> OTHER INFORMATION: PCR primer

<400> SEQUENCE: 7
ccatcgatgg gggtcatgca tcaatactat cccc                                  34

<210> SEQ ID NO 8
<211> LENGTH: 25
<212> TYPE: DNA
<213> ORGANISM: Artificial
<220> FEATURE:
<223> OTHER INFORMATION: PCR primer

<400> SEQUENCE: 8
gcttccctgt tttaatacct ttcgg                                            25

<210> SEQ ID NO 9
<211> LENGTH: 40
<212> TYPE: DNA
<213> ORGANISM: Artificial
<220> FEATURE:
<223> OTHER INFORMATION: PCR primer
```

```
<400> SEQUENCE: 9
aaaacagctg ggaggaatga ataatgagt aaagttacac                    40

<210> SEQ ID NO 10
<211> LENGTH: 40
<212> TYPE: DNA
<213> ORGANISM: Artificial
<220> FEATURE:
<223> OTHER INFORMATION: PCR primer

<400> SEQUENCE: 10
aaaacagctg ttattttgta ccgaataatc tatctccagc                    40

<210> SEQ ID NO 11
<211> LENGTH: 62
<212> TYPE: DNA
<213> ORGANISM: Artificial
<220> FEATURE:
<223> OTHER INFORMATION: PCR primer

<400> SEQUENCE: 11
aaaaggatcc aaaaggaggg attaaaatgc cacaatttgg tatattatgt aaaacaccac    60
ct                                                                  62

<210> SEQ ID NO 12
<211> LENGTH: 49
<212> TYPE: DNA
<213> ORGANISM: Artificial
<220> FEATURE:
<223> OTHER INFORMATION: PCR primer

<400> SEQUENCE: 12
aaatggcgcc gcgtacttat atgcgtctat ttatgtagga tgaaaggta         49

<210> SEQ ID NO 13
<211> LENGTH: 42
<212> TYPE: DNA
<213> ORGANISM: Artificial
<220> FEATURE:
<223> OTHER INFORMATION: PCR primer

<400> SEQUENCE: 13
aaaggatcca tgcacactca taaatttact gtaggaagtc tg                42

<210> SEQ ID NO 14
<211> LENGTH: 51
<212> TYPE: DNA
<213> ORGANISM: Artificial
<220> FEATURE:
<223> OTHER INFORMATION: PCR primer

<400> SEQUENCE: 14
ggggaggcct aaaaggggg gtcccaaata atatttgcca tagtaaccac c       51

<210> SEQ ID NO 15
<211> LENGTH: 50
<212> TYPE: DNA
<213> ORGANISM: Artificial
<220> FEATURE:
<223> OTHER INFORMATION: PCR primer

<400> SEQUENCE: 15
cccccttttt aggcctcccc tcgaacttat tagaatgatt aagattccgg        50
```

```
<210> SEQ ID NO 16
<211> LENGTH: 39
<212> TYPE: DNA
<213> ORGANISM: Artificial
<220> FEATURE:
<223> OTHER INFORMATION: PCR primer

<400> SEQUENCE: 16
aaaggatcct cattaaattt cctccatttt aagcctgtc                              39

<210> SEQ ID NO 17
<211> LENGTH: 35
<212> TYPE: DNA
<213> ORGANISM: Artificial
<220> FEATURE:
<223> OTHER INFORMATION: PCR primer

<400> SEQUENCE: 17
gtgatataat tttcctttaa atggaggagg atctg                                  35

<210> SEQ ID NO 18
<211> LENGTH: 30
<212> TYPE: DNA
<213> ORGANISM: Artificial
<220> FEATURE:
<223> OTHER INFORMATION: PCR primer

<400> SEQUENCE: 18
gccgttaata gacattataa ttccattggc                                        30

<210> SEQ ID NO 19
<211> LENGTH: 32
<212> TYPE: DNA
<213> ORGANISM: Artificial
<220> FEATURE:
<223> OTHER INFORMATION: PCR primer

<400> SEQUENCE: 19
gaattcttaa aaatatttgg atcattaagc gg                                     32

<210> SEQ ID NO 20
<211> LENGTH: 32
<212> TYPE: DNA
<213> ORGANISM: Artificial
<220> FEATURE:
<223> OTHER INFORMATION: PCR primer

<400> SEQUENCE: 20
gttgtattgg aatctttgtt attatttctc cc                                     32

<210> SEQ ID NO 21
<211> LENGTH: 38
<212> TYPE: DNA
<213> ORGANISM: Artificial
<220> FEATURE:
<223> OTHER INFORMATION: PCR primer

<400> SEQUENCE: 21
aaaaggatcc tcctgatcta ttaattcttg atgaaccc                               38

<210> SEQ ID NO 22
<211> LENGTH: 57
<212> TYPE: DNA
<213> ORGANISM: Artificial
<220> FEATURE:
<223> OTHER INFORMATION: PCR primer

<400> SEQUENCE: 22
```
ggggaggcct aaaaaggggg attgcataaa taaaaagggc tgaaaaataa atttcag       57

<210> SEQ ID NO 23
<211> LENGTH: 56
<212> TYPE: DNA
<213> ORGANISM: Artificial
<220> FEATURE:
<223> OTHER INFORMATION: PCR primer

<400> SEQUENCE: 23
cccccttttt aggcctcccc ttatttcatt cctccattgt attttttttc tatttg        56

<210> SEQ ID NO 24
<211> LENGTH: 42
<212> TYPE: DNA
<213> ORGANISM: Artificial
<220> FEATURE:
<223> OTHER INFORMATION: PCR primer

<400> SEQUENCE: 24
aaaaggatcc gctattatga ataggttaaa taagtcagct gg                       42

<210> SEQ ID NO 25
<211> LENGTH: 30
<212> TYPE: DNA
<213> ORGANISM: Artificial
<220> FEATURE:
<223> OTHER INFORMATION: PCR primer

<400> SEQUENCE: 25
aatacaagca aagagaatag gctatgtgcc                                     30

<210> SEQ ID NO 26
<211> LENGTH: 30
<212> TYPE: DNA
<213> ORGANISM: Artificial
<220> FEATURE:
<223> OTHER INFORMATION: PCR primer

<400> SEQUENCE: 26
aatacaagca aagagaatag gctatgtgcc                                     30

<210> SEQ ID NO 27
<211> LENGTH: 29
<212> TYPE: DNA
<213> ORGANISM: Artificial
<220> FEATURE:
<223> OTHER INFORMATION: PCR primer

<400> SEQUENCE: 27
ggcatatgaa gtaacaagag aaatgcagc                                      29

<210> SEQ ID NO 28
<211> LENGTH: 28
<212> TYPE: DNA
<213> ORGANISM: Artificial
<220> FEATURE:
<223> OTHER INFORMATION: PCR primer

<400> SEQUENCE: 28
ataatctatc tccagcatct ccaagacc                                       28

<210> SEQ ID NO 29
<211> LENGTH: 35
<212> TYPE: DNA
<213> ORGANISM: Artificial

```
<220> FEATURE:
<223> OTHER INFORMATION: PCR primer

<400> SEQUENCE: 29
aaaaggatcc gcagctttct ggaaggacta cggcg                          35

<210> SEQ ID NO 30
<211> LENGTH: 46
<212> TYPE: DNA
<213> ORGANISM: Artificial
<220> FEATURE:
<223> OTHER INFORMATION: PCR primer

<400> SEQUENCE: 30
ggggaggcct aaaaggggg catttactta tggtacggtt cacccc               46

<210> SEQ ID NO 31
<211> LENGTH: 55
<212> TYPE: DNA
<213> ORGANISM: Artificial
<220> FEATURE:
<223> OTHER INFORMATION: PCR primer

<400> SEQUENCE: 31
cccccttttt aggcctcccc gtctttaaaa agtaatttat caaaggcatc aaggc    55

<210> SEQ ID NO 32
<211> LENGTH: 55
<212> TYPE: DNA
<213> ORGANISM: Artificial
<220> FEATURE:
<223> OTHER INFORMATION: PCR primer

<400> SEQUENCE: 32
cccccttttt aggcctcccc gtctttaaaa agtaatttat caaaggcatc aaggc    55

<210> SEQ ID NO 33
<211> LENGTH: 29
<212> TYPE: DNA
<213> ORGANISM: Artificial
<220> FEATURE:
<223> OTHER INFORMATION: PCR primer

<400> SEQUENCE: 33
cacattgtca tttataaaag tccctaggg                                 29

<210> SEQ ID NO 34
<211> LENGTH: 29
<212> TYPE: DNA
<213> ORGANISM: Artificial
<220> FEATURE:
<223> OTHER INFORMATION: PCR primer

<400> SEQUENCE: 34
gtagtaattc caacttcaac tcttgccac                                 29

<210> SEQ ID NO 35
<211> LENGTH: 26
<212> TYPE: DNA
<213> ORGANISM: Artificial
<220> FEATURE:
<223> OTHER INFORMATION: PCR primer

<400> SEQUENCE: 35
cttagaatag ctgatattgc ttgcgg                                    26
```

```
<210> SEQ ID NO 36
<211> LENGTH: 25
<212> TYPE: DNA
<213> ORGANISM: Artificial
<220> FEATURE:
<223> OTHER INFORMATION: PCR primer

<400> SEQUENCE: 36
agcatctctc ttaatgattc tccgg                                                25
```

PROCESS FOR CHROMOSOMAL INTEGRATION AND DNA SEQUENCE REPLACEMENT IN *CLOSTRIDIA*

CROSS REFERENCE TO RELATED APPLICATIONS

This application claims priority from International Application No. PCT/EP06/066997 filed Oct. 3, 2006, the content of which is incorporated herein by reference in its entirety.

BACKGROUND OF THE INVENTION

1. Field of the Invention

The present invention is generally related to a new method for replacing or deleting DNA sequences in *Clostridia*, with high efficiency, easy to perform and applicable at an industrial level. This method is useful to modify several genetic loci in *Clostridia* in a routine manner. This method is based on a replicative vector carrying at least two marker genes.

2. Description of Related Art

*Clostridia* are gram positive, anaerobic and low GC bacteria that are widely used in industry for their capacities to produce solvents, in particular butanol, ethanol and acetone, but also diols like 1,3 propanediol, organic acids like acetic, butyric or lactic acid and vaccines.

Construction of recombinant *Clostridia* is an important part of the development in the field. *Clostridium* strains are genetically modified in order to improve their industrial capabilities.

To perform these modifications, homologous recombination is the most used technique in all kinds of organisms. Transformation and homologous recombination in several microorganisms have been extensively described in the art. See for example (Datsenko and Wanner; PNAS, 2000) and (Fabret et al., Molecular Microbiology, 2002).

*Clostridia* are not naturally transformable and currently available methods for their transformation are inefficient and do not permit the introduction of multiple mutations. This has hampered industrial developments in this field.

*Clostridia* commonly produce extracellular DNAses and restriction enzymes that degrade foreign DNA before and after introduction into the cells for transformation. Classic methods based on the introduction of PCR fragments that work well in many microorganisms such as *E. coli* or yeast, are not feasible in these organisms, since the extracellular and intracellular half life of the DNA construct to be recombined is too short and recombination efficiency is generally low. In other organisms these difficulties have been circumvented by using vectors that replicate in the host thus increasing the likelihood of the recombination event. Nevertheless after the recombination event the vector that now carries the intact target DNA sequence has to be eliminated. This problem was solved in *Lactococcus lactis* (Biswas et al, J Bacteriol., 1993) by using temperature-sensitive replicons that can be eliminated at the non-permissive temperature. No vectors with these characteristics are currently available for *Clostridia*. Therefore construction of mutants in *Clostridia* has so far been very laborious and often unsuccessful.

Inactivation of genes in *Clostridia* were reported in the following articles (see table 1).

TABLE 1

| Strain | Genotype | Reference |
|---|---|---|
| *Clostridium acetobutylicum* PJC4BK | buk−, MLS$^R$ | Green et al., 1996 |
| *Clostridium acetobutylicum* PJC4PTA | pta−, MLS$^R$ | Green et al., 1996 |
| *Clostridium acetobutylicum* PJC4AAD | aad−, MLS$^R$ | Green and Bennett, 1996 |
| *Clostridium perfringens* SM101 and F4969 | Δcpe, CatP | Sarker et al., 1999 |
| *Clostridium perfringens* Strain 13 | ΔluxS | Ohtani et al., 2002 |
| *Clostridium acetobutylicum* SKO1 | ΔspoA, MLS$^R$ | Harris et al., 2002 |
| *Clostridium perfringens* Type A | Δspo0A | Huang et al., 2004 |
| *Clostridium perfringens* SM101 | ccpA−, CatP | Varga et al., 2004 |
| *Clostridium acetobutylicum* ATCC 824 buk− | Δ SpoIIE, buk−, CatP | WO 2006/007530 |

Gene inactivation was so far performed in *Clostridia* by transforming with circular DNA that could not replicate in the target strains. Since DNAses and DNA restriction endonucleases present in *Clostridia* rapidly degrade the introduced DNA, and generally the recombination frequency in this genus is not very high, the obtention of mutants has been very laborious.

In addition, the so far described recombinant strains (see above) are all resistant to MLS or chloramphenicol and the corresponding marker genes can not be removed after the recombination event has occurred. This limits the number of possible recombinations to the number of available resistance markers in these bacteria to a maximum of 3. Furthermore, for the industrial use of these bacteria, it might be useful to have markerless strains in order to avoid the release of antibiotic resistance genes into fermentation media.

Moreover, some of these strains that have been obtained by single recombination events have the disadvantage that they are not stable if cultured without any selection pressure.

Consequently, there is still a need in the state of the art for a method for the transformation of *Clostridia* with high efficiency, with an easy step of selection of recombinant strains, that allows successive DNA sequence replacements in the same strain, leading to recombinant *Clostridia* that are genetically stable and markerless.

SUMMARY OF THE INVENTION

The present invention is related to a new method for replacing or deleting DNA sequences in *Clostridia*, easy to perform and applicable at an industrial level. This method is useful to modify several genetic loci in *Clostridia* in a routine manner.

This method is based on a replicative vector useful for the transformation of *Clostridia* with high efficiency.

An unlimited number of mutations can be introduced into the genome with this new method, by eliminating resistance cassettes from the genome and reusing them in successive rounds of DNA sequence replacement.

Efficient introduction of multiple mutations into *Clostridia* should enable industry to improve existing industrial strains and to develop new processes.

DETAILED DESCRIPTION OF THE INVENTION

The invention provides a process for the replacement of a target DNA sequence by homologous recombination in *Clostridia*, comprising:

transforming said strain with a vector comprising:
an origin of replication permitting its replication in *Clostridia*, and
a replacement cassette comprising a first marker gene surrounded by two sequences homologous to selected regions around the target DNA sequence, allowing the recombination of the cassette, and
a second marker gene,
selecting strains having integrated in their genome said cassette, that express the first marker gene,
selecting strains having eliminated said vector, that do not express the second marker gene.

All molecular biology techniques used for realizing the invention are fully described in "Molecular cloning: a laboratory manual," $2^{nd}$ edition, Cold Spring Harbor Laboratory Press, 1989, by Sambrook, Fritsch and Maniatis.

Used in the context of the present invention, the term "replacement" of a target DNA sequence means that a different sequence than the original one is introduced at the locus of the target DNA sequence.

According to the invention, a DNA sequence is defined as a gene, or an intergenic sequence. Both can comprise promoter or regulatory sequences.

The expression "target DNA sequence" means any gene, intergenic region, promoter or regulatory sequence of interest chosen by the man skilled in the art. It means in particular genes coding for proteins of interest, for example enzymes involved in the cellular metabolism.

The substituted/inserted DNA sequence may be coding or not. It may be a mutated sequence of the target gene, promoter or regulatory sequence and/or a marker such as an antibiotic resistance gene or a color generating enzyme. It may be longer or shorter than the replaced sequence, depending on the distance separating the two homologous regions.

Due to the insertion, the expression of the target gene is usually perturbed, partially or completely suppressed, or increased. The replacement of the target DNA sequence with a sequence close to the original one, but comprising mutations, leads to the actual expression of a mutated protein, promoter or regulatory sequence.

If the replacement of the target DNA sequence gives as a result a total elimination of said DNA sequence, the gene is qualified as "deleted."

The expression "homologous recombination" refers to the event of substitution of a segment of DNA by another one that possesses identical regions (homologous) or nearly so. This event is also called DNA crossover.

The term "transformation" refers to the incorporation of exogenous nucleic acid by a cell, this acquisition of new genes being transitory (if the vector carrying genes is cured) or permanent (in the case the exogenous DNA is integrated chromosomally).

The term "vector" refers to an extra-chromosomal element carrying genes or cassettes, that is usually in the form of a circular double-stranded DNA molecules, but may be a single strand DNA molecule, too. Both terms "vector" and "plasmid" are used indifferently.

The vector according to the invention is a replicative vector. It comprises at least one origin of replication, and preferentially several replicative origins, allowing it to be functional in different species.

In particular a preferred vector may comprise two replicative origins: (1) Ori, functional in *E. coli*; or (2) RepL from pIM13 issued of *B. subtilis*, functional in *Clostridia* (Mermelstein et al, Biotechnology, 1992).

The expression "sequences homologous to a target DNA sequence" refers to sequences with high sequence similarity with selected regions of the target sequence.

The term "marker gene" refers to a sequence coding for a marker protein under the control of regulatory elements functional in *Clostridia*. Such proteins are well known in the art. For example the man skilled in the art may use an antibiotic resistance gene, a fluorescent or colored marker, or a marker of auxotrophy. Examples of useful marker genes will be given below.

After the recombination event has occurred, the vector now carries the intact target DNA sequence and consequently has to be eliminated. The elimination of a replicative vector generally happens with successive cultures of clones, followed by negative or positive selection of clones having eliminated this vector. The elimination of the vector can also be an active step of the process, with the use of endonucleases that specifically cleaves DNA sequences present in the vector. Once the vector is cured, strains do not express the second marker gene anymore, and can be selected on this characteristic.

In a particular embodiment of the invention, the second marker gene is an antibiotic resistance gene. Among the useful antibiotic resistance genes, the man skilled in the art would know which is the most appropriate. For example the following genes may be used: CatP gene, giving the resistance to chloramphenicol and thiamphenicol, or $MLS^R$ gene, giving resistance to erythromycin.

In a preferred embodiment of the invention, the second marker gene is a counter-selectable marker gene.

A counter-selectable marker is a gene whose presence is lethal to the host organism under certain circumstances, such as the presence of its cognate substrate. Counter-selectable markers can be used as a positive selection for the loss of the plasmid.

Preferentially the counter-selectable marker gene is a gene that restores the activity of an absent or deleted non-essential endogenous gene.

The most-used counterselectable markers are the genes that confer sucrose, streptomycin, or fusaric acid sensitivity. They have been used to construct mutants or vaccine strains in several bacterial strains. For details see the review by Reyrat et at., 1998, Infection and Immunity. Counterselectable markers that can be used in *Clostridia* include genes giving sensitivity to 5-fluoro-uracile (5-FU), gamma-glutamyl hydrazide (GBS) or 8-aza-2,6-diaminopurine (8ADP).

In a preferred embodiment, the counter-selectable marker is the upp gene, which encodes uracil phosphoribosyl-transferase that promotes transformation of 5-fluoro-uracile (5-FU) to a toxic product. Cells having Upp activity can not grow on a 5-FU medium.

The use of this counter-selectable marker is particularly useful when the transformed *Clostridia* are Δupp, and consequently are able to grow on a medium comprising 5-FU before the transformation and after the elimination of the vector. Strains having eliminated the vector can be positively selected.

Suppressor mutants that may arise in the upp gene in the presence of 5-FU, can sometimes lead to false assumptions with respect to the loss of the plasmid. In a preferred embodiment of the invention, the vector comprises furthermore a third marker, preferentially an antibiotic resistance gene that permits a second selection of strains sensitive to the antibiotic. This negative selection may be used in addition to the positive selection based on the upp gene.

In a preferred embodiment of the invention, the vector is eliminated by digestion with endonucleases after the recombination event has occurred. Preferentially, the vector harbors DNA sequences that are recognized by restriction endonucleases and that are at the same time absent from the genome of the *Clostridium* species used. Therefore the vector is specifically destroyed without loss of integrity of the *Clostridium* genome.

Restriction endonucleases are enzymes that cleave DNA molecules at the location of specific base sequences, the restriction endonuclease site. The expert in the field will be able to determine which restriction endonuclease site is absent from the genome of the *Clostridium* strain of interest. Possible restriction endonucleases that may be applied for *C. acetobutylicum* are AscI, FseI, NotI, SfiI, SrfI. In another embodiment meganucleases, which recognize large (12-45 bp) DNA target sites, such as I-SceI, HO or I-CreI may be used.

In a preferred embodiment of the invention the *Clostridium* strain to be transformed harbors on its genome at least one endonuclease encoding gene, which recognizes the restriction endonuclease site that is present on the vector. Optionally, the restriction endonuclease expression is under the control of an inducible promoter.

An inducible promoter is a DNA element that permits the conditional expression of a target sequence by adding the corresponding inducer. For example, an inducible promoter system in *Clostridium* that is known to the expert in the field is described in Girbal et al., 2003, Appl. Env. Microbiol. 69:4985-8.

After the recombination event has occurred, and before the screening of strains that have eliminated the vector, the expression of the restriction endonuclease may be induced. The restriction endonuclease will cleave the vector present in the *Clostridia* leading to its elimination.

Optionally the restriction endonuclease encoding gene can be inserted on the genome before the introduction of the vector into the strain.

In another embodiment of the invention the restriction endonuclease encoding gene may also increase the frequency of recombination before the elimination of the plasmid by increasing the amount of linear DNA in the cells that is known to recombine better than circular DNA.

In a particular embodiment of the invention, the first marker gene is an antibiotic resistance gene introduced in the middle of the replacement cassette.

In a specific embodiment of the invention, this first marker gene may be removed from the genome of the transformed *Clostridium* strains. In particular the first marker gene may be surrounded by two recombinase target sites, and then be eliminated by action of a recombinase, after the homologous recombination event has occurred.

In an advantageous embodiment of the invention, the recombinase is expressed by a second vector carrying the corresponding gene, said vector being introduced into the *Clostridia* by transformation.

Preferentially, recombinase target sites are FRT sequences. FLP recombinase from *Saccharomyces cerevisiae* is active at a particular 34 base pair DNA sequence, termed the FRT sequence (for FLP recombinase target). When two of these FRT sites are present, the FLP enzyme creates double-stranded breaks in the DNA strands, exchanges the ends of the first FRT with those of the second target sequence, and then reattaches the exchanged strands. This process leads to deletion of the DNA which lies between the two sites.

In a specific way of performing the invention, sequences homologous to selected regions around the target DNA sequence may comprise mutations in up to 10% of the base pairs composing the DNA fragment used for the recombination event.

In an advantageous embodiment of the invention, the *Clostridium* strains to be transformed are deleted for the genes encoding restriction endonucleases. These strains present the advantage that they are readily transformable without any prior in vivo plasmid methylation.

In another advantageous embodiment of the invention, the *Clostridium* strains to be transformed are deleted for the genes encoding the extracellular DNAses.

In another embodiment of the invention, the *Clostridia* to be transformed are deleted for the upp gene.

In another advantageous embodiment of the invention the *Clostridium* strains to be transformed are chosen among *Clostridium acetobutylicum*, *Clostridium bejeirinckii*, *Clostridium saccharoperbutylacetonicum*, *Clostridium butylicum*, *Clostridium butyricum*, *Clostridium perfringens*, *Clostridium tetani*, *Clostridium sporogenes*, *Clostridium thermocellum*, *Clostridium saccharolyticum* (now *Thermoanaerobacter saccharolyticum*), *Clostridium thermosulfurogenes* (now *Thermoanaerobacter thermosulfurigenes*), *Clostridium thermohydrosulfuricum* (now *Thermoanaerobacter ethanolicus*).

The preferred *Clostridium* strain is *Clostridium acetobutylicum*.

In a preferred embodiment of the invention, the *Clostridium acetobutylicum* strain to be transformed is a strain Δ Cac15, deleted for the gene encoding for the restriction endonuclease Cac 824I. This strain presents the advantage that it is readily transformable without any prior in vivo plasmid methylation.

In another preferred embodiment of the invention, the *Clostridium acetobutylicum* strain to be transformed is a strain whose upp gene was deleted, termed Δ upp. As a consequence the transformation of the strain with a vector carrying the upp gene allows the selection of strains sensible to 5-FU medium, and then the positive selection of strains having lost the plasmid that are not sensible to 5-FU medium anymore.

The *Clostridium acetobutylicum* strain to be transformed can also be Δ Cac 15 Δ upp.

The process is advantageously used for successive replacement of two or more target genes by homologous recombination in the same *Clostridium* strain.

The present invention also concerns a recombinant *Clostridium* strain susceptible to be obtained by the process according to the invention. Advantageously, the process according to the invention may be used to obtain recombinant *Clostridium* strains wherein the gene cac15 was deleted strain Δ cac15), wherein the gene upp was deleted (strain Δ upp) and wherein both genes cac15 and upp were deleted (strain Δ Cac15 Δ upp).

The present invention also concerns the vector for transforming the strain, such as described above.

The following steps are successively performed:

A—Amplification of two selected regions around the target DNA sequence; 1, 2, 3, 4 represent PCR primers B—Cloning of obtained PCR fragments into the cloning vector pTOPO C—Insertion of a marker at the StuI restriction site, present in the PCR primers D—Cloning of the replacement cassette at the BamHI site of pCONS 2.1: construction of pREP clo Y vector E—Transformation of *Clostridium* with pREP cloY vector F—Chromosomal integration of replacement cassette by double crossover during subculture G—Screening of clones with $Ery^R$ and $Thiam^S$ phenotypes H—PCR analysis to check for gene replacement and plasmid loss

OR

D'—Cloning of the replacement cassette at the BamHI site of pCONS::UPP: Construction of pREP do Y:UPP vector E'—Transformation of *Clostridium* Δupp with pREP cloY:UPP vector F'—Chromosomal integration of replacement cassette by double crossover during subculture G'—Screening of clones with $Ery^R$ and $5\text{-}FU^R$ ($Thiam^S$) phenotypes H'—PCR analysis to check for gene replacement and plasmid loss.

EXAMPLES

Example 1

Construction of Vectors 1.1 Construction of pUC18-FRT-MLS2

Figure 1:
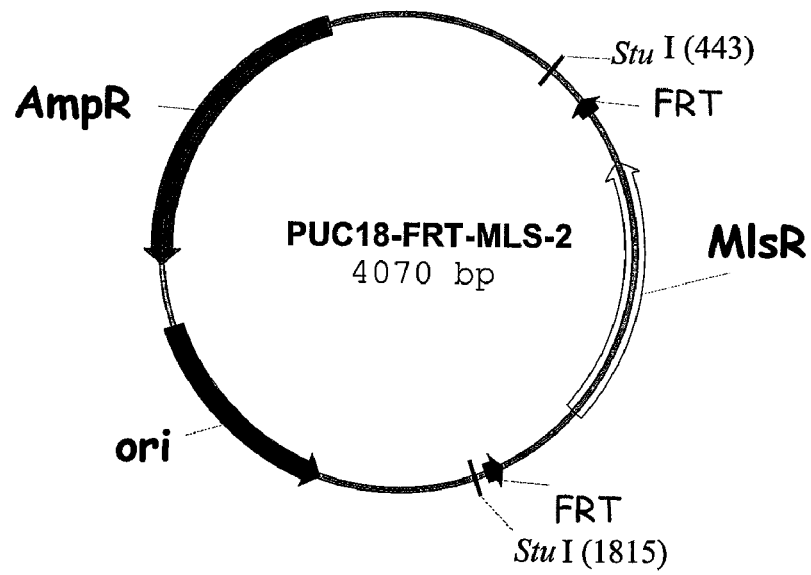
FIG. 1: Map of the pUC18-FRT-MLS2 vector

This plasmid contains an $MLS^r$ gene functional in *Clostridia* and flanked by two FRT sites and two StuI sites and is useful for the construction of the replacement cassettes. Inverse polymerase chain reaction (IPCR) was performed with Pwo DNA polymerase with pKD4 as a template plasmid (Datsenko and Wanner, 2000) and oligonucleotides PKD4.1 and PKD4.2 as primers to amplify the plasmid region with the FRT sites but without the $Km^r$ marker. This blunt end fragment was later ligated to the MLSr gene obtained after a HindIII digestion of the pETSPO plasmid (Harris et al, 2002, J. Bacteriol) and Klenow treatment. The corresponding plasmid (pKD4-Ery1) was then used as a template to amplify the $MLS^r$ gene flanked by two FRT sites and two StuI sites in a PCR reaction using the oligonucleotides FRT-MLSR-F and FRT-MLSR-R as primers and Pwo DNA polymerase. This fragment was directly cloned into the SmaI digested pUC18 to yield the pUC18-FRT-MLS2 plasmid (FIG. 1).

```
Pcr primers:
PKD4.1 (SEQ ID N°1):
5'-ctggcgccctgagtgcttgcggcagcgtgagggg-3'

PKD4.2 (SEQ ID N°2):
5'-agcccggggatctcatgctggagttcttcgccc-3'

FRT-MLSR-F (SEQ ID N°3):
5'-tacaggccttgagcgattgtgtaggctggagc-3'

FRT-MLSR-R (SEQ ID N°4):
5'-aacaggcctgggatgtaacgcactgagaagccc-3'
```

1.2 Construction of pCons 2.1

Figure 2:
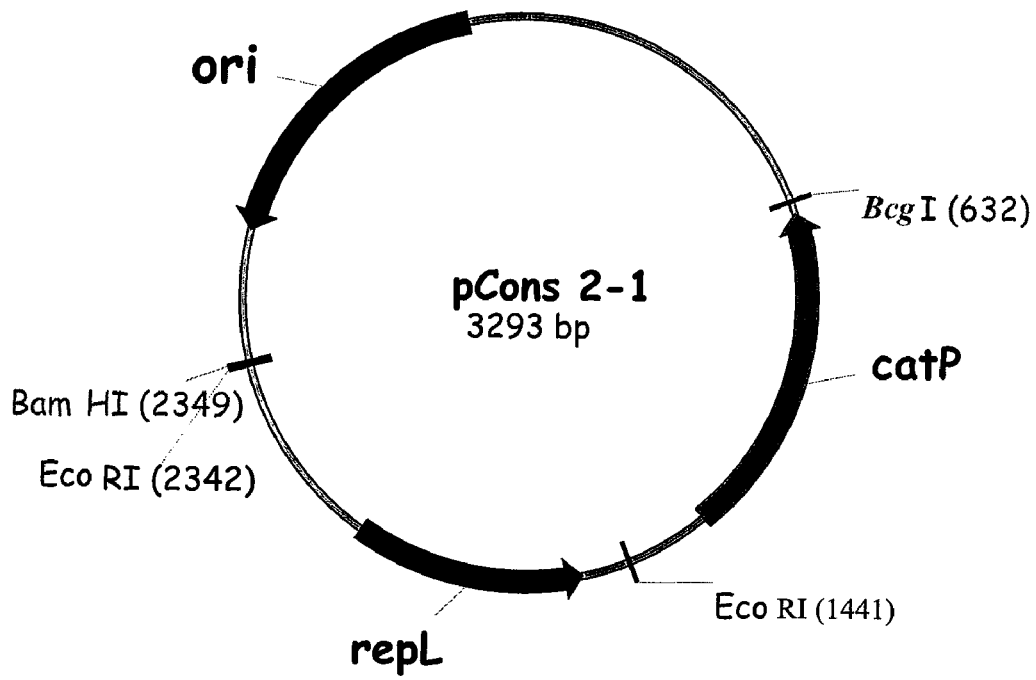
FIG. 2: Map of the pCons2-1 vector.

This plasmid contains a pIM13 origin of replication functional in *Clostridia* (rolling circle mechanism of replication), a catP gene conferring resistance to thiamphenicol and a unique BamHI site for the cloning of the replacement cassette. This plasmid was constructed in a two step procedure from the pETSPO plasmid (Harris et al, 2002, J. Bacteriol) to remove part of a polylinker and among others a BamHI and an EcoRI site. IPCR was performed with Pwo DNA polymerase with pETSPO as a template plasmid and oligonucleotides PCONSAccI and PCONSEcoRI as primers, and the PCR product was phosphorylated and ligated. After transformation of *E. coli* the pCons0 plasmid was obtained. This plasmid was then digested with BamHI to remove the spo0A cassette, the proper DNA fragment purified and ligated to yield plasmid pCons2-1. The map of pCons2-1 is given in FIG. 2.

```
PCR primers:
PCONSAccI (SEQ ID N°5):
5'- ccggggtaccgtcgacctgcagcc -3'

PCONSEcoRI (SEQ ID N°6):
5'- gaattccgcgagctcggtacccggc -3'
```

1.3 Construction of the pCIP 2-1 Vector

Figure 3:
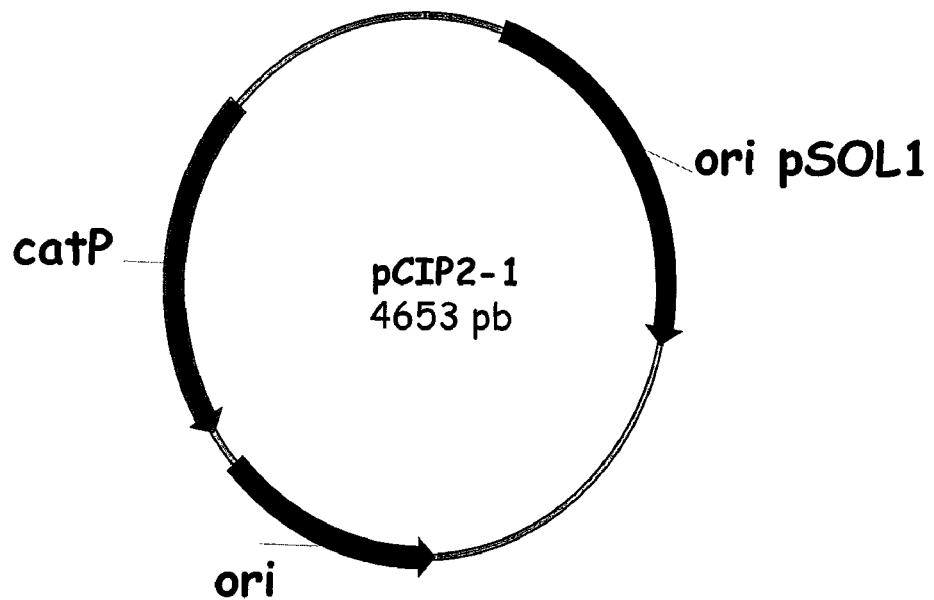
FIG. 3: Map of the pCIP2-1 vector

In this construction the pIM13 origin of replication from pCons2-1 was replaced by the origin of replication of the pSOL1 plasmid, a plasmid having a ☐ mechanism of replication. For this purpose the origin of replication of pSOL1 was PCR amplified with Pwo DNA polymerase using total DNA of *C. acetobutylicum* as a template and oligonucleotides ori-3-D and ori-4-R as primers. This PCR product was cloned in the pCR-BluntII-TOPO and the resulting plasmid digested by EcoRI and the 2.2 kb fragment was purified. Similarly the pCons2.1 plasmid was digested by EcoRI and the 2.4 kb fragment purified and ligated to the 2.2 kb EcoRI fragment containing the origin of replication of pSOL1 to yield the plasmid pCIP2-1 (FIG. 3).

```
Pcr primers:
ORI-3-D (SEQ ID N°7):
5'-ccatcgatgggggtcatgcatcaatactatcccc-3'

ORL-4-R (SEQ ID N°8):
5'-gcttccctgttttaataccttttcgg-3'
```

1.4 Construction of the pCons::upp Vector

The upp gene with its own ribosome bindind site (rbs) was cloned into pCons2.1 at the BcgI site just downstream of the CatP gene in order to construct an artificial operon with upp expressed under the control of the CatP promoter. In this way, no homologous regions were introduced that would allow chromosomal integration of the upp gene in the Δcac15Δupp strain in further deletion experiments, which use the upp gene as a counter selectable marker for plasmid loss.

Figure 4:
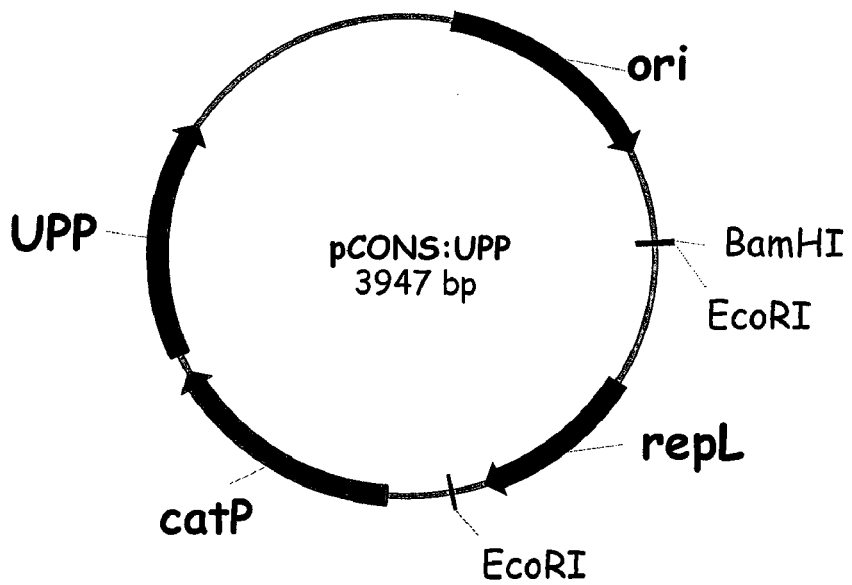
FIG. 4: Map of the pCons::UPP vector

The upp gene with its rbs was PCR (Pfu) amplified from genomic *C. acetobutylicum* DNA using oligonucleotides REP-UPP F et REP-UPP R as primers. The 664 bp PCR-product was digested by PvuII and cloned into pCons2.1 digested by BcgI and treated with T4 DNA Polymerase to blunt ends. In this way the pCons::UPP (see FIG. 4) replicative vector was obtained.

```
PCR primers:
REP-UPP F (SEQ ID N°9):
5'- aaaacagctgggaggaatgaaataatgagtaaagttacac-3'

REP-UPP R (SEQ ID N°10):
5'- aaaacagctgttattttgtaccgaataatctatctccagc-3'
```

1.5 Construction of the pCLF1 Vector

The FLP1 gene of *S. cerevisiae* coding for the FLP recombinase was cloned in the pCons2.1 vector under the control of the promoter and RBS from the thiolase (thl) gene from *C. acetobutylicum* permitting high expression in this organism.

The FLP1 gene was PCR (Pfu) amplified using the FLP1-D and FLP1-R oligonucleotides as primers and the pCP20 plasmid (Datsenko and Wanner, 2000) as a template.

```
PCR primers:
FLP1-D (SEQ ID N°11):
5'- aaaaggatccaaaaggagggattaaaatgccacaatttggtatatt
atgtaaaacaccacct-3'

FLP1-R (SEQ ID N°12):
5'- aaatggcgccgcgtacttatatgcgtctatttatgtaggatgaaag
gta-3'
```

FLP1-D has a 5' extension including a BamHI site and the RBS sequence of thl.

FLP1-R introduced an SfoI site in 3' of the PCR product.

The PCR product was digested by BamHI and SfoI and directly cloned into the pSOS95 expression vector that had been digested with the same enzymes, giving the pEX-FLP1 (6281pb) plasmid.

Figure 5:
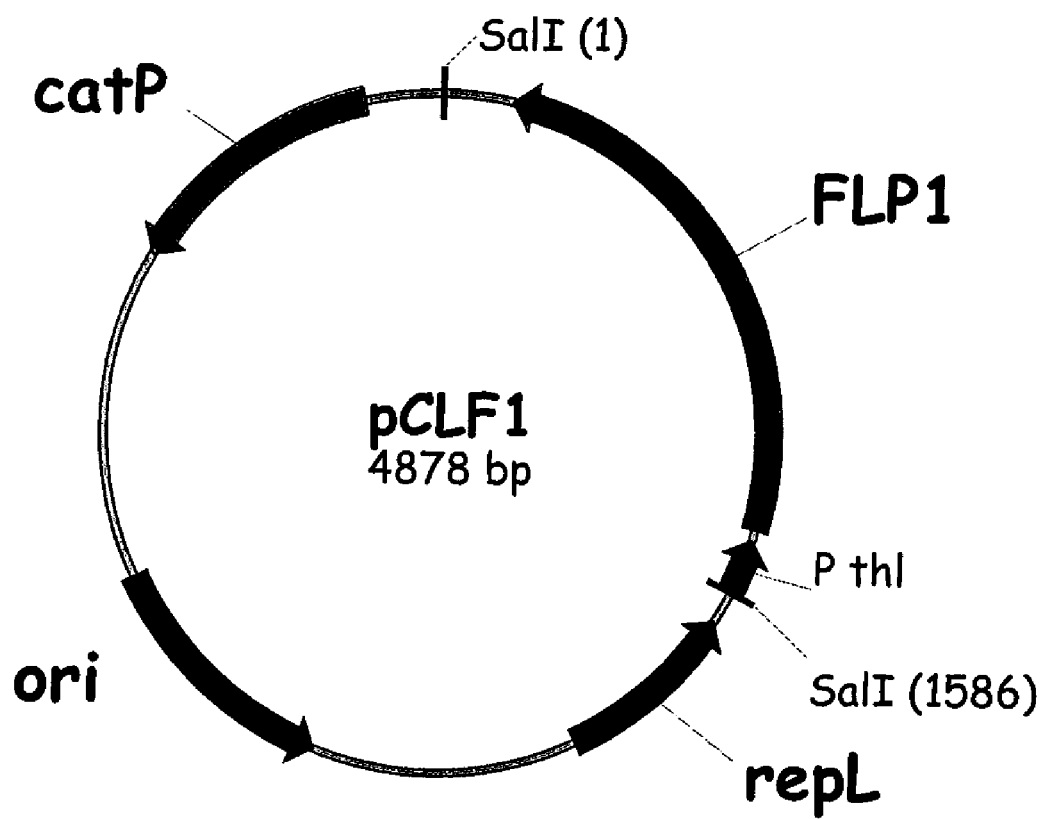
FIG. 5: Map of the pCLF1 vector

The SalI fragment (1585pb) of pEX-FLP1 containing the FLP1 expression cassette was cloned at the SalI site of pCONS2.1 to obtain the pCLF1 (4878pb) plasmid (FIG. 5).

Example 2

Deletion of the cac1502 Gene Encoding the cac824I Restriction Enzyme in *Clostridium acetobutylicum*

Figure 6:
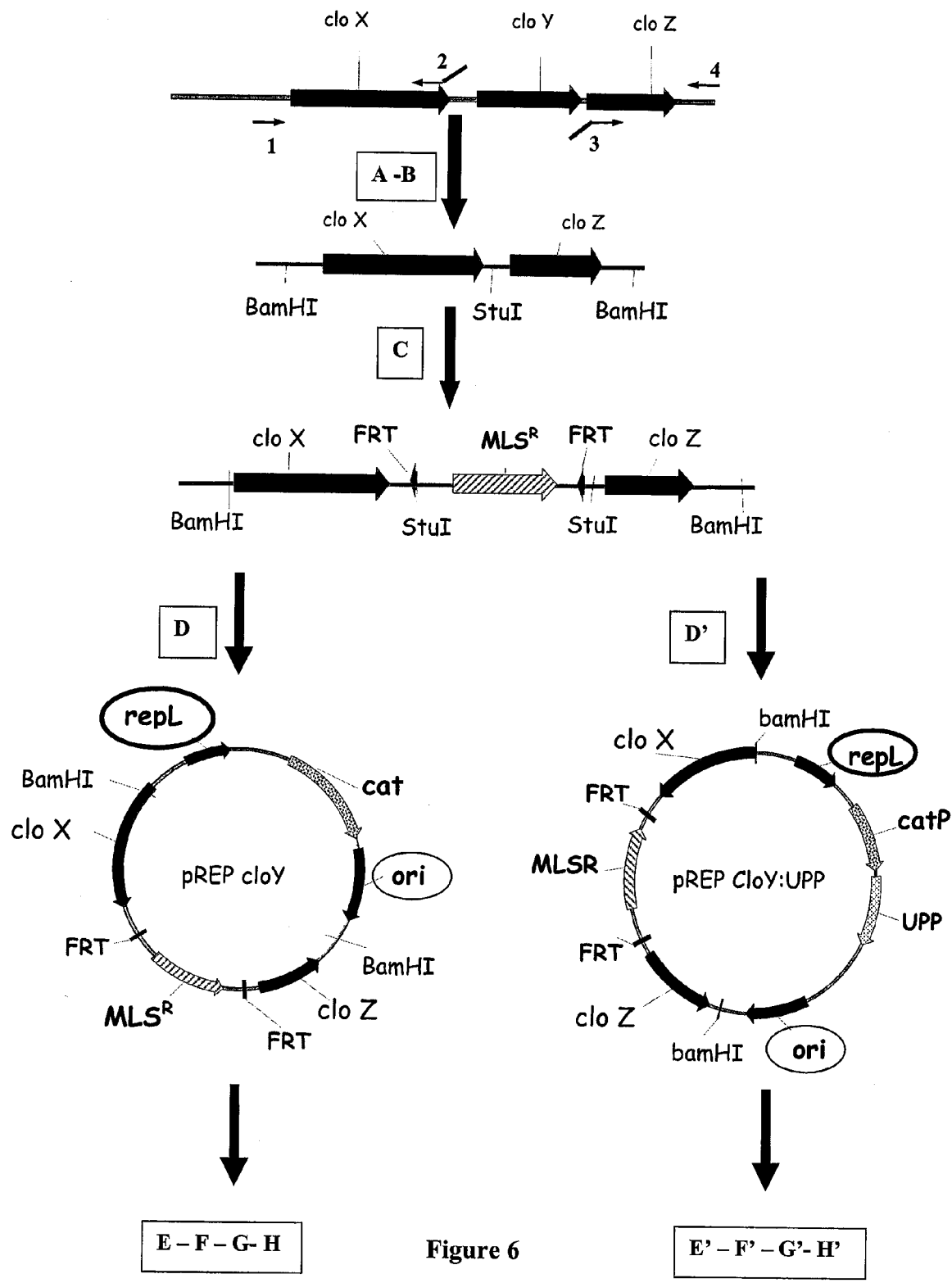
FIG. 6: Schematic representation of the deletion method for *Clostridia*.

See FIG. 6 for a schematic representation of the method.

Two DNA fragments surrounding the Cac824I encoding gene (CAC1502) were PCR amplified with Pwo DNA polymerase using total DNA from *C. acetobutylicum* as template and two specific pairs of oligonucleotides as primers (see table 2). Using pairs of primers CAC 1B-CAC 2 and CAC 3-CAC 4B, 1493 bp and 999 bp DNA fragments were obtained, respectively. Both primers CAC 1B and CAC 4B introduce a BamHI site while primers CAC 2 and CAC 3 have complementary 5' extended sequences which introduce a StuI site. DNA fragments CAC 1B-CAC 2 and CAC 3-CAC 4B were joined in a PCR fusion experiment with primers CAC 1B and CAC 4B and the resulting fragment was cloned in the pCR4-TOPO-Blunt vector to yield pTOPO:cac15. At the unique StuI site of pTOPO:cac15, the 1372 bp StuI fragment of pUC18-FRT-MLS2 harboring the antibiotic resistance MLS$^r$ gene with FRT sequences on both sides was introduced. The cac1502 replacement cassette obtained after BamHI digestion of the resulting plasmid was cloned, at the BamHI, into pCons2-1 site to yield the pREPCAC15 plasmid and into pCIP2.1 to yield pCIPCAC15.

The pREPCAC15 and pCIPCAC15 plasmids were methylated in vivo and used to transform *C. acetobutylicum* by electroporation. After selection on Petri plates for clones resistant to erythromycin (40 µg/ml), one colony of each transformants was cultured for 24 hours in liquid synthetic medium with erythromycin at 40 µg/ml and then subcultured in liquid 2YTG medium without antibiotic. Appropriate dilutions were plated on reinforced *Clostridium* agar (RCA) with erythromycin at 40 µg/ml. To select integrants having lost pREPCAC15 or pCIPCAC15 vectors, erythromycin resistant clones were replica plated on both RCA with erythromycin at 40 µg/ml and RCA with thiamphenicol at 50 µg/ml. While several colonies with the desired phenotype were obtained with the pREPCAC15 transformants, no such colonies were obtained with the pCIPCAC15 transformants. This demonstrates that the Δ mechanism of replication of pCIPCAC15 is less favorable in promoting double crossover in *C. acetobutylicum* than a rolling circle mechanism. The genotype of clones resistant to erythromycin and sensitive to thiamphenicol was checked by PCR analysis (with primers CAC 0 and CAC 5 located outside of the CAC15 replacement cassette and primers CAC D and CAC R located inside of cac1502). Δ cac15::mls$^R$ strains which have lost pREPCAC15 were isolated.

A Δ cac15::mls$^R$ strain was transformed with the pCLF1 vector expressing the FLP1 gene encoding the Flp recombinase from *S. cerevisiae*. After transformation and selection for resistance to thiamphenicol (50 µg/ml) on Petri plates, one colony was cultured on synthetic liquid medium with thiamphenicol at 50 µg/ml and appropriate dilutions were plated on RCA with thiamphenicol at 50 µg/ml. Thiamphenicol resistant clones were replica plated on both RCA with erythromycin at 40 µg/ml and RCA with thiamphenicol at 50 µg/ml. The genotype of clones with erythromycin sensitivity and thiamphenicol resistance was checked by PCR analysis with primers CAC 0 and CAC 5B.

Two successive 24 hours cultures of the Δ cac15 strain with erythromycin sensitivity and thiamphenicol resistance were carried out in order to loose pCLF1. The Δ cac15 strain which has lost pCLF1 was isolated according to its sensitivity to both erythromycin and thiamphenicol. The strain was called *C. acetobutylicum* MGC Δ cac15.

TABLE 2

| Name | SEQ ID N° | Primer sequences |
|---|---|---|
| CAC 1B | 13 | aaaggatccatgcacactcataaatttactgtaggaagtctg' |
| CAC 2 | 14 | ggggaggcctaaaaaggggggtcccaaataatatttgccatagtaaccacc |
| CAC 3 | 15 | cccccttttaggcctcccctcgaacttattagaatgattaagattccgg |
| CAC 4B | 16 | aaaggatcctcattaaatttcctccattttaagcctgtc |
| | | |
| CAC 0 | 17 | gtgatataattttcctttaaatggaggaggatctg |
| CAC 5B | 18 | gccgttaatagacattataattccattggc |
| CAC D | 19 | gaattcttaaaaatatttggatcattaagcgg |
| CAC R | 20 | gttgtattggaatctttgttattatttctccc |

Example 3

Deletion of the upp Gene Encoding the Uracil Phosphoribosyl-Transferase in Clostridium acetobutylicum Δcac15

Two DNA fragments upstream and downstream of upp (CAC2879) were PCR amplified with Pwo DNA polymerase using total DNA from *C. acetobutylicum* as template and two specific pairs of oligonucleotides as primers (see table 3). With the primer pairs UPP 1-UPP 2 and UPP 3-UPP 4, 1103 bp and 1105 bp DNA fragments were obtained, respectively. Both primers UPP 1 and UPP 4 introduce a BamHI site, while primers UPP 2 and UPP 3 have 5' extended sequences which introduce a StuI site. DNA fragments UPP 1-UPP 2 and UPP 3-UPP 4 were joined in a PCR fusion experiment with primers UPP 1 and UPP 4 and the resulting fragment was cloned in pCR4-TOPO-Blunt to yield pTOPO:upp. At the unique StuI site of pTOPO:upp, the 1372 bp StuI fragment of pUC18-FRT-MLS2 harboring the antibiotic resistance MLS$^r$ gene with FRT sequences on both sides was introduced. The upp replacement cassette obtained after BamHI digestion of the resulting plasmid was cloned into pCons2-1 at the BamHI site to yield the pREPUPP plasmid.

The plasmid pREPUPP was used to transform *C. acetobutylicum* MGCΔcac15 strain by electroporation without previous in vivo methylation. After selection on Petri plates for clones resistant to erythromycin (40 μg/ml), one colony was cultured for 24 hours in liquid synthetic medium with erythromycin at 40 μg/ml and then subcultured in liquid 2YTG medium without antibiotic. Appropriate dilutions were plated on RCA with erythromycin at 40 μg/ml. To select integrants having lost the pREPUPP vector, erythromycin resistant clones were replica plated on both RCA with erythromycin at 40 μg/ml and RCA with thiamphenicol at 50 μg/ml. The genotype of clones resistant to erythromycin and sensitive to thiamphenicol was checked by PCR analysis (with primers UPP 0 and UPP 5 located outside of the UPP replacement cassette and primers UPP D and UPP R located inside of UPP). The Δcac15Δupp::mls$^R$ strain that has lost pREPUPP was isolated. The previous cac1502 deletion was confirmed as previously described in the first example. The Δ cac15Δ upp::mls$^R$ strain is resistant to 400 μM 5-FU compared to 50 μM for the Δ cac15 strain.

The Δcac15Δupp::mls$^R$ strain was transformed with the pCLF1 vector expressing the FLP1 gene encoding the Flp recombinase from *S. cerevisiae*. After transformation and selection for resistance to thiamphenicol (50 μg/ml) on Petri plates, one colony was cultured in synthetic liquid medium with thiamphenicol at 50 μg/ml and appropriate dilutions were plated on RCA with thiamphenicol at 50 μg/ml. Thiamphenicol resistant clones were replica plated on both RCA with erythromycin at 40 μg/ml and RCA with thiamphenicol at 50 μg/ml. The genotype of clones with erythromycin sensitivity and thiamphenicol resistance was checked by PCR analysis with primers UPP 0 and UPP 5. Two successive 24 hours cultures of the Δ cac15 Δ upp strain with erythromycin sensitivity and thiamphenicol resistance were carried out in order to lose pCLF1. The Δ cac15 Δ upp strain that has lost pCLF1 was isolated by determining its sensitivity to both erythromycin and thiamphenicol.

TABLE 3

| Name | SEQ ID N° | Primer sequences |
|---|---|---|
| UPP 1 | 21 | aaaaggatcctcctgatctattaattcttgatgaaccc |
| UPP 2 | 22 | ggggaggcctaaaaaggggattgcataaataaaaagggctgaaaaataaatttcag |
| UPP 3 | 23 | ccccctttttaggcctcccctttatttcattcctccattgtattttttttctatttg |
| UPP 4 | 24 | aaaaggatccgctattatgaataggttaaataagtcagctgg |
| UPP 0 | 25 | aatacaagcaaagagaataggctatgtgcc |
| UPP 5 | 26 | aatacaagcaaagagaataggctatgtgcc |
| UPP D | 27 | ggcatatgaagtaacaagagaaatgcagc |
| UPP R | 28 | ataatctatctccagcatctccaagacc |

Example 4

Deletion of the cac3535 Gene with the Use of upp and 5-Fluorouracil as a Positive Selection for Plasmid Loss Two DNA fragments upstream and downstream of cac3535 gene encoding a second restriction-modification system of *C. acetobutylicum* were PCR amplified with Pwo DNA polymerase using total DNA from *C. acetobutylicum* as template and two specific pairs of oligonucleotides (see table 4). With the primer pairs RM 1-RM 2 and RM 3-RM 4, 1 kbp and 0.9 kbp DNA fragments were obtained, respectively. Both primers RM 1 and RM 4 introduce a BamHI site, while primers RM 2 and RM 3 have complementary 5' extended sequences that introduce a StuI site. DNA fragments RM 1-RM 2 and RM 3-RM 4 were joined in a PCR fusion experiment using primers RM 1 and RM 4 and the resulting fragment was cloned in pCR4-TOPO-Blunt vector to yield the pTOPO:cac3535 plasmid. At the unique StuI site of pTOPO:cac3535, the 1372 bp StuI fragment of pUC18-FRT-MLS2 harboring the antibiotic resistance MLS$^r$ gene with FRT sequences on both sides was introduced. The CAC3535 replacement cassette obtained after BamHI digestion of the resulting plasmid was cloned into pCons::upp at the BamHI site to yield the pREPCAC3535::upp plasmid.

The pREPCAC3535::upp plasmid was used to transform the *C. acetobutylicum* MGCΔcac15 Δ upp strain by electroporation. After selection for erythromycin (40 μg/ml) resistant clones on Petri plates, one colony was cultured for 24 hours in liquid synthetic medium with erythromycin at 40 μg/ml and 100 Δ l of undiluted culture were plated on RCA with erythromycin at 40 μg/ml and 5-FU at 400 μM. Colonies resistant to both erythromycin and 5-FU were replica plated on both RCA with erythromycin at 40 μg/ml and RCA with thiamphenicol at 50 μg/ml to verify that 5-FU resistance is associated with thiamphenicol sensitivity. The genotype of clones resistant to erythromycin and sensitive to thiamphenicol was checked by PCR analysis (with primers RM 0 and RM 5 located outside of the cac3535 replacement cassette and primers RM D and RM R located inside of cac3535 gene). In this way the Δ cac15ΔuppΔcac35::mls$^R$ strain that has lost pREPCAC3535::upp was isolated.

TABLE 4

| Name | SEQ ID N° | Primer sequences |
|------|-----------|------------------|
| RM 1 | 29 | aaaaggatccgcagctttctggaaggactacggcg |
| RM 2 | 30 | ggggaggcctaaaaaggggggcatttacttatggtacggttcaccccc |
| RM 3 | 31 | cccccttttttaggcctccccgtctttaaaaagtaatttatcaaaggcatcaaggc |
| RM 4 | 32 | cccccttttttaggcctccccgtctttaaaaagtaatttatcaaaggcatcaaggc |
| RM 0 | 33 | cacattgtcatttataaaagtccctaggg |
| RM 5 | 34 | gtagtaattccaacttcaactcttgccac |
| RM D | 35 | cttagaatagctgatattgcttgcgg |
| RM R | 36 | agcatctctcttaatgattctccgg |

Bennett G N, Scotcher M C BLOCKING SPORULATION BY INHIBITING SPOIIE WO2006007530 published on 2006 Jan. 19 Applicant: RICE UNIVERSITY (US)

Biswas I, Gruss A, Ehrlich S D, Maguin E. High-efficiency gene inactivation and replacement system for gram-positive bacteria. J Bacteriol. 1993 June; 175(11):3628-35.

Datsenko K A, Wanner B L. One-step inactivation of chromosomal genes in *Escherichia coli* K-12 using PCR products. Proc Natl Acad Sci USA. 2000 Jun. 6; 97(12):6640-5.

Fabret C, Ehrlich S D, Noirot P. A new mutation delivery system for genome-scale approaches in *Bacillus subtilis*. Mol Microbiol. 2002 October; 46(1):25-36.

Girbal L, Mortier-Barriere I, Raynaud F, Rouanet C, Croux C, Soucaille P. Development of a sensitive gene expression reporter system and an inducible promoter-repressor system for *Clostridium acetobutylicum*. Appl Environ Microbiol. 2003 August; 69(8):4985-8.

Green E M, Bennett G N. Inactivation of an aldehyde/alcohol dehydrogenase gene from *Clostridium acetobutylicum* ATCC 824. Appl Biochem Biotechnol. 1996 Spring; 57-58:213-21.

Green E M, Boynton Z L, Harris L M, Rudolph F B, Papoutsakis E T, Bennett G N. Genetic manipulation of acid formation pathways by gene inactivation in *Clostridium acetobutylicum* ATCC 824. Microbiology. 1996 August; 142 (Pt 8):2079-86.

Harris L M, Welker N E, Papoutsakis E T. Northern, morphological, and fermentation analysis of spo0A inactivation and overexpression in *Clostridium acetobutylicum* ATCC 824. J Bacteriol. 2002 July; 184(13): 3586-97.

Huang I H, Waters M, Grau R R, Sarker M R. Disruption of the gene (spo0A) encoding sporulation transcription factor blocks endospore formation and enterotoxin production in enterotoxigenic *Clostridium perfringens* type A. FEMS Microbiol Lett. 2004 Apr. 15; 233(2):233-40.

Mermelstein L D, Welker N E, Bennett G N, Papoutsakis E T. Expression of cloned homologous fermentative genes in *Clostridium acetobutylicum* ATCC 824. Biotechnology (NY). 1992 February; 10(2): 190-5.

Ohtani K, Hayashi H, Shimizu T. The luxS gene is involved in cell-cell signalling for toxin production in *Clostridium perfringens*. Mol Microbiol. 2002 April; 44(1):171-9.

Reyrat J M, Pelicic V, Gicquel B, Rappuoli R. Counterselectable markers: untapped tools for bacterial genetics and pathogenesis. Infect Immun. 1998 September; 66(9):4011-7. Review.

Sarker M R, Carman R J, McClane B A. Inactivation of the gene (cpe) encoding Clostridium perfringens enterotoxin eliminates the ability of two cpe-positive *C. perfringens* type A human gastrointestinal disease isolates to affect rabbit ileal loops. Mol Microbiol. 1999 September; 33(5): 946-58. Erratum in: Mol Microbiol 2000 January; 35(1): 249.

Varga J, Stirewalt V L, Melville S B. The CcpA protein is necessary for efficient sporulation and enterotoxin gene (cpe) regulation in *Clostridium perfringens*. J Bacteriol. 2004 August; 186(16):5221-9.

We claim:

1. A process for the replacement of a target DNA sequence by homologous recombination in *Clostridia*, wherein the process comprises the following steps:
    transforming a strain with a vector comprising
        an origin of replication permitting its replication in *Clostridia*, and
        a replacement cassette comprising a first marker gene surrounded by two sequences homologous to selected regions around the target DNA sequence, allowing the recombination of the cassette, and
        a second marker gene,
    selecting strains having integrated in their genome said cassette that express the first marker gene, and
    selecting strains having eliminated said vector that do not express the second marker gene,
    wherein the second marker gene is the upp gene and wherein said upp gene is a counter-selectable marker.

2. The process according to claim 1, wherein said vector comprises a third marker that permits a negative selection of strains having eliminated said vector.

3. The process according to claim 1, wherein the vector is eliminated by digestion with endonucleases.

4. The process according to claim 3 wherein the vector harbors DNA sequences that are recognized by restriction endonucleases and are at the same time absent from the genome of the used *Clostridium* strain.

5. The process according to claim 3, wherein the *Clostridium* strain harbors on its genome at least one endonuclease, specific for restriction sites present in said vector, optionally expressed under the control of an inducible promoter.

6. The process according to claim 4, wherein the *Clostridium* strain harbors on its genome at least one gene coding for an endonuclease, specific for restriction sites present in the vector, said gene being optionally expressed under the control of an inducible promoter.

7. The process according to claim 1, wherein the first marker gene is an antibiotic resistance gene.

8. The process according to claim 1, wherein the first marker gene is surrounded by two recombinase target sites.

9. The process according to claim 7, wherein the first marker gene is eliminated by the action of a recombinase after the homologous recombination event has occurred.

10. The process according to claim 9, wherein said recombinase is expressed by a gene carried by a second vector introduced into the strain.

11. The process according to claim 9, wherein said recombinase target sites are FRT sequences, and said recombinase is the FLP recombinase.

12. The process according to claim 1, wherein the *Clostridia* to be transformed are deleted for cac1502 encoding the cac824I restriction enzyme.

13. The process according to claim 1, wherein the *Clostridia* to be transformed are deleted for cac3535 encoding a restriction enzyme.

14. The process according to claim 1, wherein the *Clostridia* to be transformed are deleted for upp gene.

15. The process according to claim 1, wherein the *Clostridium* strains are chosen among *Clostridium acetobutylicum*, *Clostridium bejeirinckii*, *Clostridium saccharoperbutylacetonicum*, *Clostridium butylicum*, *Clostridium butylicum*, *Clostridium perfringens*, *Clostridium tetani*, *Clostridium sporogenes*, *Clostridium thermocellum*, *Clostridium saccharolyticum* (now *Thermoanaerobacter saccharolyticum*), *Clostridium thermosulfurogenes* (now *Thermoanaerobacter thermosulfurigenes*), *Clostridium thermohydrosulfuricum* (now *Thermoanaerobacter ethanolicus*).

16. The process according to claim 15 wherein the *Clostridium* strain is *Clostridium acetobutylicum*.

17. The process according to claim 16, wherein the *Clostridium acetobutylicum* strain to be transformed is Δcac1502.

18. The process according to claim 16, wherein the *Clostridium acetobutylicum* strain to be transformed is Δupp.

19. The process according to claim 16, wherein the *Clostridium acetobutylicum* strain to be transformed is Δcac1502 Δupp.

20. The process for replacement of two or more target genes by homologous recombination in a same *Clostridium* strain, wherein the process according to claim 1 is performed successively two or more times.

* * * * *